(12) United States Patent
Ritrivi et al.

(10) Patent No.: US 11,331,215 B2
(45) Date of Patent: May 17, 2022

(54) IMPLANTABLE THERMAL THERAPY DEVICES

(71) Applicant: Medicool Technologies Inc., Rochester, MN (US)

(72) Inventors: Charles Ritrivi, Houston, TX (US); Richard Scott Sanders, San Juan Capistrano, CA (US); Gregory J. Seifert, Saint Paul, MN (US)

(73) Assignee: Medicool Technologies Inc., Rochester, MN (US)

( * ) Notice: Subject to any disclaimer, the term of this patent is extended or adjusted under 35 U.S.C. 154(b) by 348 days.

(21) Appl. No.: 16/012,200

(22) Filed: Jun. 19, 2018

(65) Prior Publication Data

US 2018/0360652 A1   Dec. 20, 2018

Related U.S. Application Data

(60) Provisional application No. 62/521,622, filed on Jun. 19, 2017.

(51) Int. Cl.
  *A61F 7/12* (2006.01)
  *A61F 7/00* (2006.01)
  *F25B 21/02* (2006.01)

(52) U.S. Cl.
  CPC .............. *A61F 7/12* (2013.01); *A61F 7/007* (2013.01); *A61F 2007/008* (2013.01); *A61F 2007/0075* (2013.01); *A61F 2007/0078* (2013.01); *A61F 2007/0096* (2013.01); *A61F 2007/126* (2013.01); *F25B 21/02* (2013.01); *F25B 2400/24* (2013.01)

(58) Field of Classification Search
  CPC .............................................. A61F 2007/0075
  See application file for complete search history.

(56) References Cited

U.S. PATENT DOCUMENTS

| | | | |
|---|---|---|---|
| 5,529,067 A | 6/1996 | Larsen et al. | |
| 7,840,264 B1 | 11/2010 | Mower | |
| 7,996,982 B2 * | 8/2011 | Darley | A61N 1/0541 29/592.1 |
| 9,318,681 B2 * | 4/2016 | Gavillet | H01L 23/4275 |
| 2006/0241707 A9 | 10/2006 | Mower | |
| 2008/0168775 A1 | 7/2008 | Windheim et al. | |
| 2008/0172073 A1 * | 7/2008 | Boyden | A61F 2/02 606/155 |

(Continued)

OTHER PUBLICATIONS

Fujii, "Focal brain cooling: revisiting a potential therapeutic option for intractable epilepsy", Bill. Yamaguchi Med. Sch. 59 (3-4): 35-41, 2012.

(Continued)

*Primary Examiner* — Kaitlyn E Smith
(74) *Attorney, Agent, or Firm* — Fish & Richardson P.C.

(57) ABSTRACT

Implantable thermal therapy devices, systems, and methods are provided for the treatment of pathological conditions including arrhythmias and trauma. The implantable thermal therapy devices and systems are specifically structured to deliver transient cooling to a target tissue, and to gradually dissipate the heat energy transferred from the target tissue to other body masses in a controlled and delicate manner. In some examples, a phase change material can be used to accomplish such a gradual dissipation of the heat.

20 Claims, 2 Drawing Sheets

(56) References Cited

U.S. PATENT DOCUMENTS

| | | | |
|---|---|---|---|
| 2008/0195161 A1 | 8/2008 | Sakuma et al. | |
| 2008/0208286 A1* | 8/2008 | Kieval | A61N 1/36071 607/46 |
| 2008/0262341 A1* | 10/2008 | Boyden | A61F 2/06 600/424 |
| 2008/0264464 A1* | 10/2008 | Lee | A61F 7/007 136/201 |
| 2010/0198204 A1* | 8/2010 | Rogers | A61F 7/007 606/21 |
| 2010/0217356 A1* | 8/2010 | Bikson | A61N 1/08 607/63 |
| 2012/0310313 A1* | 12/2012 | Rogers | A61F 7/007 607/113 |
| 2013/0090700 A1* | 4/2013 | Kieval | A61N 1/36135 607/3 |
| 2013/0226267 A9* | 8/2013 | Bikson | G01R 33/288 607/63 |
| 2013/0253626 A1* | 9/2013 | Kieval | A61N 1/36071 607/116 |
| 2014/0163664 A1* | 6/2014 | Goldsmith | A61B 17/12181 623/1.11 |
| 2014/0233184 A1 | 8/2014 | Thompson et al. | |
| 2014/0309750 A1 | 10/2014 | Kelley et al. | |
| 2015/0223971 A1* | 8/2015 | Zaveri | A61F 7/007 607/113 |
| 2018/0360650 A1* | 12/2018 | Asirvatham | A61B 18/1402 |

OTHER PUBLICATIONS

Hoffman and Cranfield, "Electrophysiology of the Heart", The Atrium, 71-73, 95-99, 109, 112, 114, 129, 191-193, 286-289, 1970.
International Search Report and Written Opinion in Application No. PCT/US2018/038266, dated Aug. 24, 2018, 13 pages.
Witt et al., External Cooling of the Myocardium Slows Electrical Conduction and Terminates Atrial Fibrillation, vol. 69, issue 11,2 pages, 2017 (abstract).
Witt et al., "Termination of AF with Epicardial Cooling", 24 pages, Jan. 25, 2018.
Yambe et al., "New implantable therapeutic device for the control of an atrial fibrillation attack using the Peltier element" 34th Annual Conference of the IEEE EMBS, 5741-5744, 2012.
International Preliminary Report on Patentability Application No. PCT/US2018/038266 dated Dec. 24, 2019, 7 pages.

* cited by examiner

IMPLANTABLE THERMAL THERAPY DEVICES

CROSS-REFERENCE TO RELATED APPLICATIONS

This application claims priority to U.S. Application Ser. No. 62/521,622, filed on Jun. 19, 2017. The disclosure of the prior application is considered part of the disclosure of this application, and is incorporated in its entirety into this application.

BACKGROUND

1. Technical Field

This document relates to devices and methods for delivering cooling therapy. For example, this document relates to implantable thermal therapy devices and methods for the use of such implantable thermal therapy devices.

2. Background Information

Thermoelectric cooling uses the Peltier effect to create a heat flux between the junction of two different types of materials. Such thermoelectric cooling devices, also referred to as Peltier devices, are typically solid state devices that operate based upon the Seebeck effect. Generally, Peltier devices are constructed using two parallel plates of ceramic with N-P junctions. When electric current is applied, one plate increases in temperature and the opposite plate is cooled. These thermoelectric cooling devices have found conventional applications in the contexts of chillers, cooling computer chips, portable coolers, and the like.

To date, Peltier devices have not been used in medical applications where cooling requires the Peltier device to be implanted in the body and exposed to blood or body fluids.

SUMMARY

This document describes devices and methods for delivering tissue-cooling therapy. For example, this document describes implantable thermal therapy devices and methods for use thereof. The thermal therapy devices can be implanted temporarily or permanently. In one example implementation, the implantable thermal devices described herein can be used to treat pathological conditions including cardiac arrhythmias using tissue temperature modulation via the implantable thermal devices. For example, the devices and methods described herein can be used to treat atrial and/or ventricular fibrillation by cooling the epicardium, endocardium, and/or nerves leading to or from the heart. While the use of the implantable thermal therapy devices described herein is sometimes described in the context of treating cardiac arrhythmias, it should be understood that other therapeutic uses are also envisioned such as, but not limited to, treating brain trauma, appetite suppression, treatment for ischemia, cooling post-surgery (e.g., to lessen pain and swelling), treatment of seizure disorders, Parkinson's disorders, stroke, drownings, hypothermia, hyperthermia, head trauma, and heating or cooling during surgery.

This disclosure describes implantable devices that deliver non-destructive rapid and temporary cooling of tissues, such as cardiac tissues for the termination (and potentially prevention) of atrial arrhythmias. In some embodiments, the system is capable of temporarily cooling tissues in a controlled fashion by any desired amount, up to about 20 degrees Celsius (or colder in some cases). The use of non-freezing cold is particularly attractive due to its well-established safety record in cardiac applications. In some embodiments, the system will be constructed of a single thermal electric cooling element that uses the Peltier effect to create a heat differential between opposing surfaces. In some embodiments, the system will be constructed of an array of electrically interconnected thermal electric cooling elements that use the Peltier effect to create a heat differential between opposing surfaces. While some embodiments are deployed epicardially, the scope of this disclosure also includes endocardial options, intravenous options (e.g., as in or around blood vessels), and other therapeutic implementations. In some implementations, a pulsed-mode operation will allow quick attainment and short duration cooling that will terminate atrial fibrillation.

The implantable thermal therapy devices and systems described herein are specifically structured to deliver transient cooling to a target tissue, and to gradually dissipate the heat energy transferred from the target tissue to other body masses (including, in some cases, blood being circulated in the patient) in a controlled and delicate manner. As described further below, in some embodiments a heat sink that includes a phase change material can be advantageously used to accomplish such a gradual dissipation of the heat.

The implantable thermal therapy devices and systems may also include an energy source, such as a battery or an inductive energy receiver. The energy source may be configured to operate in a pulse-mode for providing energy to the heat pump. The implantable thermal therapy devices and systems may also include one or more temperature monitoring devices. The one or more temperature monitoring devices may include thermocouples, thermistors, and the like. The implantable thermal therapy devices and systems may also include one or more controllers.

In one aspect, this disclosure is directed to an implantable medical device for providing thermal therapy. The implantable medical device includes an enclosure; a heat pump located within the enclosure; and a heat sink located within the enclosure and comprising a phase change material and a thermally conductive interface structure positioned between the heat pump and the phase change material.

Such an implantable medical device for providing thermal therapy may optionally include one or more of the following features. The thermally conductive interface structure may include a plate and a plurality of columns extending from the plate and into the phase change material. The device may also include a battery and a control processor located within the enclosure. The heat pump may be electrically coupled to a separate implantable device containing a battery and a control processor. The device may also include an insulative barrier between the heat sink and the enclosure. One side of the heat pump may be thermally coupled via a low thermal resistance means with the enclosure. At least one portion of the enclosure may be thermally insulated from one or more other portions of the enclosure. One side of the heat pump may be thermally coupled via a low thermal resistance means with the thermally conductive interface structure. The heat pump may comprise a Peltier device. One side of the Peltier device may be thermally coupled with the thermally conductive interface structure. The device may also include an insulative barrier extending between a periphery of the Peltier device and the enclosure. The enclosure may be hermetically sealed. The device may also include one or more electrical leads electrically coupled to the heat pump and extending from the enclosure. The device may also include one or more thermal sensors configured to detect tissue temperature. The enclosure may include a non-planar contoured outer surface. The device may also include a sensing mechanism configured for detecting when to activate the heat pump.

In another aspect, this disclosure is directed to a method for delivering therapeutic cooling to a target tissue of a patient. The method includes: (i) cooling at least a portion of an outer surface of a thermal therapy device implanted within the patient to a first temperature that is lower than a body temperature of the target tissue, wherein the cooled outer surface of the thermal therapy device is in contact with the target tissue such that heat is transferred from the target tissue to the cooled outer surface, wherein the cooling of the outer surface is generated by a Peltier device located within the implanted thermal therapy device; and (ii) absorbing, in a phase change material located within the implanted thermal therapy device, at least some of the heat transferred from the target tissue.

Such a method for delivering therapeutic cooling may also include one or more of the following features. The target tissue may be an atrial tissue surface or a ventricle tissue surface. Absorbing the at least some of the heat transferred from the target tissue in the phase change material may cause at least some of the phase change material to change phases from a solid to a liquid.

Particular embodiments of the subject matter described in this document can be implemented to realize one or more of the following advantages. First, transient therapeutic tissue cooling therapy can be delivered using the devices and methods described herein. In some embodiments, the therapeutic tissue cooling can advantageously be delivered using a system that is fully implantable and self-contained. Accordingly, the patient receiving treatment can be fully ambulatory, and can experience a lifestyle that is relatively unhindered by the presence of the implantable therapeutic cooling device. In some embodiments, heart conditions such as arrhythmias and others can be treated using the devices and methods provided herein. In some embodiments, arrhythmias can be treated relatively painlessly. In some cases, such conditions can be treated in a minimally invasive fashion using the devices and methods provided herein. Such minimally invasive techniques can reduce recovery times, patient discomfort, and treatment costs.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

Like reference numbers represent corresponding parts throughout.

DETAILED DESCRIPTION

Figure 1:
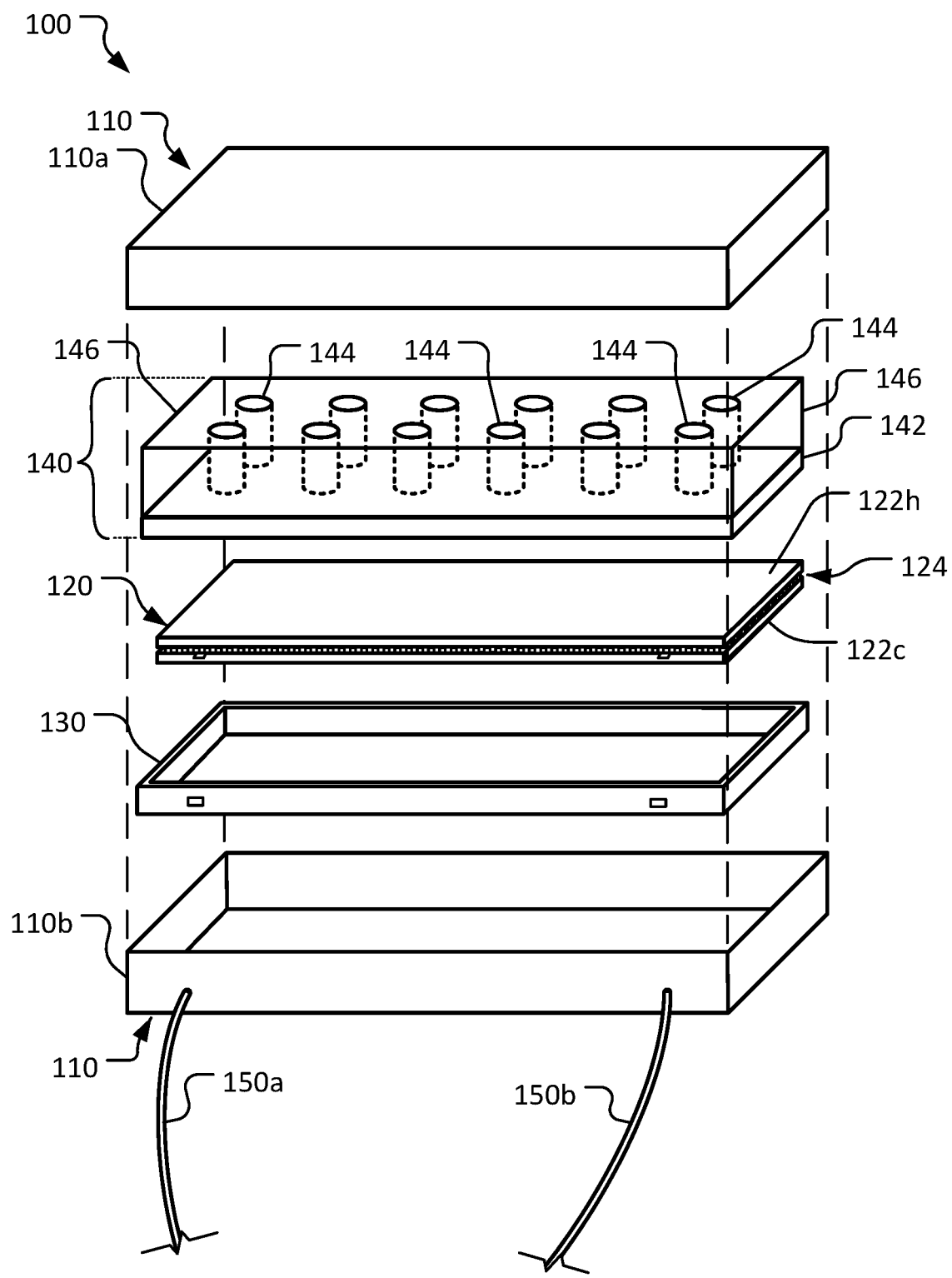
FIG. 1 is a perspective, exploded diagram of an example implantable thermal therapy device in accordance with some embodiments provided herein.

This document describes devices and methods for delivering tissue-cooling therapy. For example, this document describes implantable thermal therapy devices and methods for use thereof. The thermal therapy devices can be implanted temporarily or permanently. In one example implementation, the implantable thermal devices described herein can be used to treat pathological conditions including, but not limited to, cardiac arrhythmias using tissue temperature modulation via the implantable thermal devices. While the use of the implantable thermal therapy devices described herein is generally described in the context of treating cardiac arrhythmias, it should be understood that other therapeutic uses are also envisioned such as, but not limited to, treating brain trauma, treatment for ischemia, appetite suppression, cooling post-surgery (e.g., to lessen pain and swelling), treatment of seizure disorders, Parkinson's disorders, stroke, drownings, hypothermia, hyperthermia, head trauma, and heating or cooling during surgery.

The implantable thermal therapy devices described herein a heat pump that may include one or more thermoelectric cooling elements that use the Peltier effect to create a heat flux between the junction of two different types of materials. In contrast to the more commonly used vapor-compression refrigeration, Peltier cooling elements require no moving parts or circulating refrigerants, have a near infinite life, and can be made of a small size and flexible shape. These elements become thermally active when an electrical current is applied across them, with the temperature differential being a function of the current supplied into the system.

In some embodiments, the implantable thermal therapy devices may include an array of multiple Peltier elements that are inter-joined to create a functional "cooling mesh." In particular embodiments, a single Peltier element may be implanted. The Peltier elements are scalable to any desired size and can be configured in various shapes and form factors. In some embodiments, the implantable thermal devices described herein can be implanted minimally-invasively. Alternatively, in some embodiments the devices provided herein are surgically placed.

The challenge of implanting a Peltier element in a human body and delivering cooling therapy therefrom engenders various complicating factors. First, Peltier elements will tend to short out and fail when exposed to conductive fluids such as salt water. Since, a majority of the weight of a human body is comprised of salt water, the Peltier elements will need to be isolated from body fluids when implanted in the human body. Second, when Peltier elements are used to cool tissue, some means of removing the heat from the opposite side of the Peltier element plate is required, while also preventing patient pain or tissue damage from exposure to the increasing temperature due to the heating. As described herein, the inventors have developed solutions to the aforementioned technical challenges.

Referring to FIG. 1, an example implantable thermal therapy device 100 can be implanted in a human body to deliver therapeutic transient tissue cooling. Implantable thermal therapy device 100 is specifically structured to use a heat pump to deliver transient cooling to a target tissue, and to gradually dissipate the heat energy transferred from the target tissue to other body masses in a controlled and gentle manner. As described further below, a phase change material can be used to absorb the heat generated by the thermal therapy device and subsequently facilitate the gradual dissipation of the heat in a safe and effective manner.

The depicted embodiment of implantable thermal therapy device 100 (shown here in an exploded assembly view for enhanced visualization of the internal components) includes a hermetically sealable enclosure 110 made of enclosure portions 110a and 110b, a Peltier element 120 (an example type of a heat pump), an insulative barrier 130, a heat exchange module 140 (a type of heat sink), and electrical leads 150a and 150b. The Peltier element 120, insulative barrier 130, and heat exchange module 140 are each hermetically sealed within enclosure 110. Electrical leads 150a and 150b extend from enclosure 110 to a DC power source from which electrical energy is supplied to operate Peltier element 120. In some embodiments, implantable thermal therapy device 100 includes a battery module, a controller, and/or one or more physiologic sensors in, or coupled to, enclosure 110.

The heat pump used as part of the depicted implantable thermal therapy device 100 is Peltier element 120. In some embodiments, other types of heat pumps can be used. In keeping with the typical construction of Peltier elements, Peltier element 120 includes a hot side 122h, and a cold side 122c. The hot side 122h and the cold side 122c are physically separated from each other and interconnected with each other by an array of alternating n-type and p-type semiconductors 124. The different types of semiconductors 124 have complementary Peltier coefficients. Semiconductors 124 are soldered between hot side 122h and cold side 122c, such that semiconductors 124 are electrically in series and thermally in parallel. As DC electric current flows through Peltier element 120 (via electrical leads 150a-b that are electrically connected to Peltier element 120), heat from cold side 122c is transferred to hot side 122h, so that cold side 122c gets cooler while hot side 122h gets hotter.

In the depicted embodiment, the peripheral edges of Peltier element 120 are insulated from enclosure 110 by insulative barrier 130. Insulative barrier 130 can be just an electrical insulator, or just a thermal insulator, or both an electrical and a thermal insulator. Insulative barrier 130 can be made of any suitable insulative material such as, but not confined to, Teflon®, phenolic cast resins, nylon, glass and the like. In some embodiments, insulative barrier 130 also acts to hold Peltier element 120 in place so that cold side 122c stays in direct contact with enclosure portion 110b while also leaving a space between the edges to allow for welding shut of enclosure portions 110a and 110b. In some embodiments, cold side 122c is thermally coupled with enclosure portion 110b via a low thermal resistance material/structure positioned between cold side 122c and the inner wall surface of enclosure portion 110b.

Peltier element 120 is hermetically sealed within enclosure 110 to protect Peltier element 120 from body fluid ingress. Any biologically inert, highly heat conductive metal can be used to construct enclosure 110 such that Peltier element 120 is isolated from body fluids. Such a biologically inert, highly conductive metal for enclosure 110 can include, but is not limited to, titanium, titanium alloys, stainless steel, stainless steel alloys, 316 stainless steel, and the like, and combinations thereof. In some embodiments, enclosure portions 110a and 110b are welded closed in a hermetically sealed fashion. Enclosure 110 is also equipped with a means of allowing electrical leads 150a and 150b to exit enclosure 110 through glass feedthroughs, for example.

While the depicted embodiment of implantable thermal therapy device 100 includes a rectangular enclosure 110, it should be understood that other form factors are also envisioned. For example, in some embodiments enclosure 110 has contoured surfaces rather than planar surfaces. In some such embodiments, enclosure 110 can be specifically contoured to interface with a particular patient's anatomy.

Electrical leads 150a and 150b can be connected to a source of DC energy for Peltier element 120. In some embodiments, a battery module (not shown) is implanted under the patient's skin and electrical leads 150a and 150b are connected thereto. Such a battery module can also include a controller and/or one or more physiologic sensors in, or coupled to, the same enclosure as the battery module. In particular embodiments, electrical leads 150a and 150b are connected to a coil that is implanted under the patient's skin and that is configured to inductively receive DC energy from a coupleable primary coil that can be located external to the patient, either transiently or on an on-going basis. During operation of implantable thermal therapy device 100, some or all of the outer surface of enclosure portion 110b will become cooled by virtue of its thermal contact with cold side 122c of Peltier element 120. In some embodiments, the actual portion of enclosure portion 110b in contact or thermal communication with cold side 122c is thermally insulated from other portions of enclosure portion 110b (and enclosure portion 110a). The cooled portion of enclosure portion 110b can be placed into contact with the target tissue (e.g., the epicardium, in the example of cardiac therapy).

As described herein, while Peltier element 120 cools on cold side 122c (and enclosure portion 110b), the other side (hot side 122h) of Peltier element 120 heats up. Some dissipating or managing of the heat on hot side 122h is needed to prevent injury to the tissues in contact with enclosure 110a (the hot side of implantable thermal therapy device 100). Heat exchange module 140 is specifically designed for this purpose.

The heat sink of implantable thermal therapy device 100 (i.e., heat exchange module 140) is constructed so that heat is initially absorbed and then subsequently released to body tissues (or blood, other body fluids, etc.) in contact with enclosure 110a gradually, such that the temperature of enclosure 110a (the hot side of implantable thermal therapy device 100) is not significantly above body temperature. In some embodiments, the heat sink is designed to keep the hot side exposed to body tissue below 50 degrees centigrade, and more ideally closer to 40 degrees centigrade. Accordingly, implantable thermal therapy device 100 is configured to permit rapid cooling without injury to the patient's tissues in contact with the hot side, and without the need for external cooling fins or other heat dissipation mechanisms.

Again, the implantable use of thermal therapy device 100 includes the utilization of heat exchange module 140 that interfaces with hot side 122h of Peltier device 120 through direct contact or via a thermally conductive interface material/structure. The heat exchange module 140 also interfaces with enclosure 110a (the hot side of implantable thermal therapy device 100). In some embodiments, one or more portions of heat exchange module 140 is in direct contact with one or more inner wall portions of enclosure 110 (e.g., enclosure portion 110a). In some embodiments, an insulative barrier is positioned between one or more portions of heat exchange module 140 and one or more inner wall portions of enclosure 110.

In the depicted embodiment, the thermally conductive interface structure of heat exchange module 140 includes a plate 142 and a plurality of columns 144 extending from plate 142. In some embodiments, plate 142 and columns 144 may be constructed of very highly thermally conductive materials (e.g., having a thermal conductivity of k=200 to 300 W/m-deg C. or higher), such as Annealed Pyrolytic Graphite (APG) or other highly conductive material alloy structures to accelerate heat transfer from hot side 122h of Peltier device 120 into heat exchange module 140. The heat exchange module 140 (being constructed of APG or other highly conductive material) is designed to rapidly conduct the heat from the hot side 122h of Peltier device 120, and to evenly distribute the heat through the PCM 146 (since the PCM 146 itself typically will have a very low thermal conductivity). While columns 144, as depicted, have circular cross-sectional shapes, in some embodiments columns 144 have other cross-sectional shapes such as, but not limited to, triangular, rectangular, polygonal, ovular, star-shaped, and the like. While the depicted embodiment includes twelve columns 144, in some embodiments one, two, three, four, five, six, seven, eight, nine, ten, eleven, thirteen, fourteen, fifteen, sixteen, seventeen, eighteen, nineteen, twenty, or more than twenty columns 144 are included. Heat exchange module 140 also includes a phase change material (PCM) 146.

PCM 146 is in contact with plate 142 and in contact with the plurality of columns 144. In the depicted embodiment, the plurality of columns 144 extend into PCM 146.

In some embodiments, PCM 146 is made of a material with a melting temperature in the range of between human body core temperature (37° C.) and 50° C. PCMs that are applicable due to their high specific heat, high heat of fusion and melting temperature in the range of about 37° C. and 50° C. include, but are not limited to, paraffins. In some embodiments, PCM 146 has a very low thermal conductivity (e.g., k=0.2 W/m-deg C.). Some desirable characteristics of PCM 146 are low volume change with phase change, no toxicity, no corrosivity, and compatibility with the material of enclosure 110.

A particular desirable property of PCM 146 is that it absorbs heat while exhibiting a minimal rise in temperature. In some embodiments, PCM 146 can absorb heat without exhibiting a sensible temperature rise as it changes phase from solid to liquid, or liquid to vapor. In particular embodiments, PCM 146 is capable of absorbing more than twice the heat energy of non-PCMs that do not undergo phase change. Two additional properties of PCM 146 are high specific heat (Cp) and high heat of fusion (h). Specific heat is the amount of heat a material can absorb per unit mass. Heat of fusion is the amount of heat a material can absorb per unit mass without a sensible temperature increase (at constant temperature) while undergoing a change of phase, for example, transitioning from a solid to a liquid, or a liquid or solid to a gas (vapor).

The heat sink and heat exchange structures/properties of implantable thermal therapy device 100 involves three main components: (i) the metal enclosure 110, (ii) PCM 146, and (iii) the thermally conductive interface of heat exchange module 140 (which includes plate 142 and the plurality of columns 144 extending from plate 142) that is interfaced with hot side 122h of Peltier device 120. In some embodiments, columns 144 may consist of rods or fins designed to efficiently and rapidly transport the heat from plate 142 and hot side 122h into PCM 146. In some embodiments, columns 144 may extend into PCM 146 between approximately the midpoint of heat exchange module 140 to the very top of the thickness of PCM 146 (or just short thereof).

Figure 2:
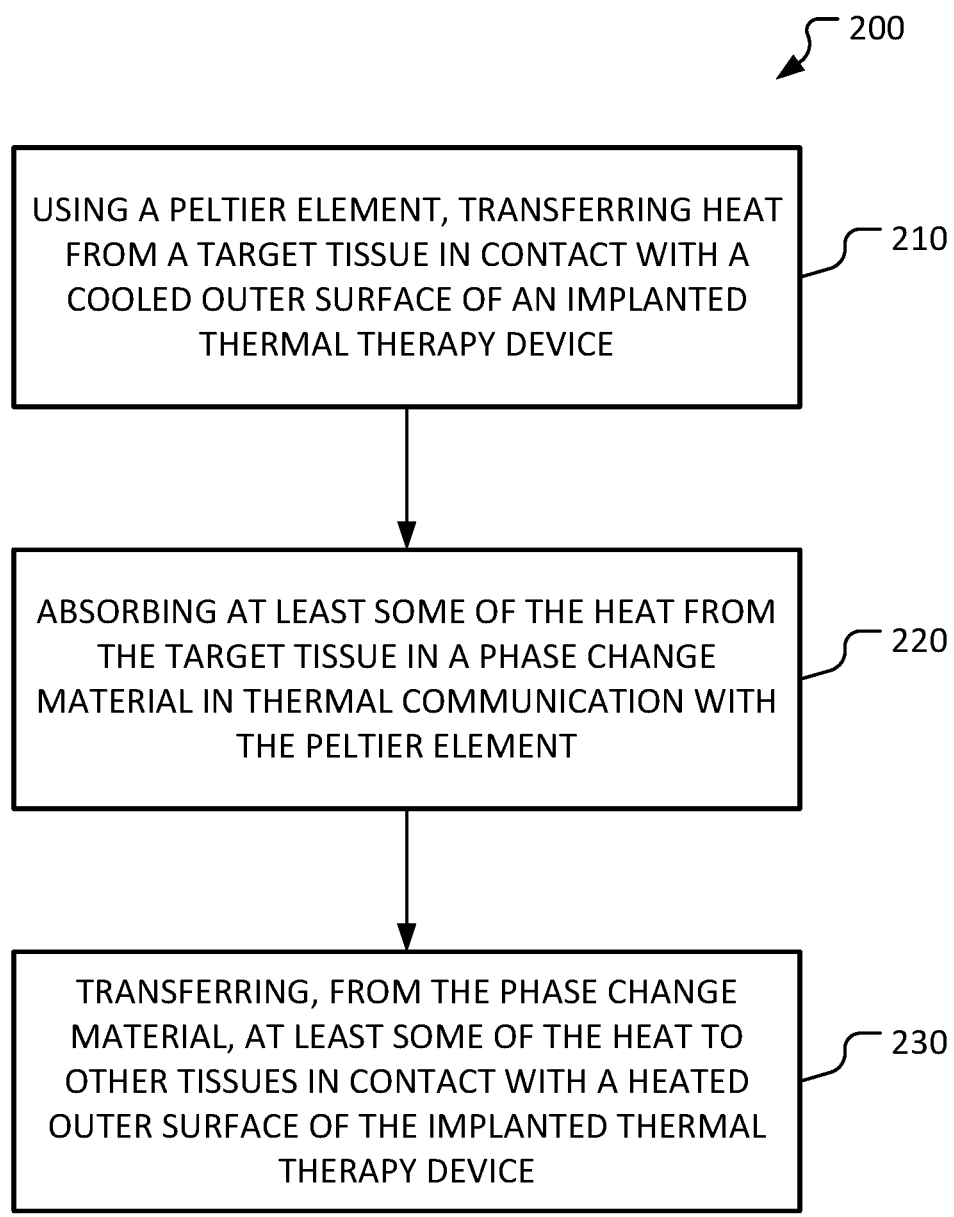
FIG. 2 is a flowchart of a method for delivering tissue cooling therapy in accordance with some embodiments provided herein.

FIG. 2 is a flowchart of a method 200 for delivering tissue cooling therapy to a target tissue of a patient, in accordance with some embodiments provided herein. In some embodiments, the method 200 can be performed by, or using, the implantable thermal therapy device 100 described herein.

In step 210, a Peltier element in an implanted thermal therapy device is used to cool an outer surface of the thermal therapy device to temperature that is lower than a body temperature of the target tissue. The thermal therapy device is implanted in the patient such that the cooled outer surface of the thermal therapy device is in contact with the target tissue. Accordingly, the target tissue in contact with the cooled outer surface of the implanted thermal therapy device is cooled, and the heat is transferred to the opposite side of the thermal therapy device. In some embodiments, the cooling delivered in step 210 is transient (discontinuous), and may be cyclical. For example, in some embodiments the cooling may be delivered in a range of time from 10 seconds to 40 seconds, or 30 seconds to 60 seconds, or 50 seconds to 90 seconds, or 80 seconds, to 110 seconds, or 100 seconds to 130 seconds, or 1 minute to 3 minutes, or 2 minutes to 4 minutes, or 3 minutes to 5 minutes, of 4 minutes to 6 minutes, or 5 minutes to 7 minutes, or 6 minutes to 8 minutes, or 7 minutes to 10 minutes, or more than 10 minutes.

In step 220, a phase change material (PCM) located within the implanted thermal therapy device absorbs at least some of the heat transferred from the target tissue. For example, in the context of implantable thermal therapy device 100 described herein, heat from the target tissue is transferred from Peltier device 120 to heat exchange module 140 (that includes the PCM 146). The PCM absorbs the heat, and in some cases some or all of the PCM changes phase from solid to liquid, for example.

In step 230, at least some of the heat absorbed by the PCM is subsequently released and transferred to other tissues (or blood and/or other body fluids) in contact with the heat releasing side of the outer surface of the implanted thermal therapy device. The heat is transferred at a slower rate than it was absorbed by the PCM during the cooling of the target tissue that took place in step 210. Accordingly, step 230 can generally take longer than step 210. In some embodiments, the duration of step 230 in comparison to the duration of step 210 is about 2:1, or about 3:1, or about 4:1, or more than 4:1. The heat is transferred in a non-destructive manner (at a temperature that does not cause tissue damage). That is, the outer surfaces of enclosure 110 will not exceed 55° C. (the temperature that has been demonstrated to cause irreversible tissue damage). Ideally, the temperature of the outer surfaces of enclosure 110 will be maintained at levels that will be imperceptible to the patient.

Additional Optional Features

In some embodiments provided herein, implantable thermal therapy device 100 includes temperature monitoring devices (e.g., integrated thermocouples, thermistors, or other types of temperature monitoring devices) for temperature registration and feedback.

In some embodiments, implantable thermal therapy device 100 can be affixed to a non-biodegradable fabric to permit surgical suturing of thermal therapy device 100 to target tissues or to increase friction with adjacent tissues.

In some embodiments, the devices and methods and methods described herein can be used for defibrillation utilizing cold. For example, this document provides devices and methods for treating ventricular fibrillation (VF) by cooling the epicardium. As explained elsewhere herein, the devices and methods provided herein can also be used to treat other disorders by applying heating and/or cooling to a patient (internally and/or externally) in a number of different advantageous manners.

In some embodiments, the cooling module is patient activated. In some embodiments, the cooling module is activated automatically if one or more conditions is/are detected (e.g., by sensors in communication with the implanted thermal therapy device) that indicate that providing tissue cooling will be beneficial to the patient.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An implantable medical device for providing thermal therapy to a target tissue, the device comprising:
    a hermetically sealed enclosure comprising:
        a first enclosure portion comprising an outer hot surface of the device; and
        a second enclosure portion comprising an outer cold surface of the device,
        wherein the first and second enclosure portions are welded to each other to form the enclosure, and
        wherein an interior space is defined within the enclosure;
    a heat pump located within the interior space defined within the enclosure and including a hot side and a cold side; and
    a heat sink located within the interior space defined within the enclosure and comprising:
        a phase change material; and
        a thermally conductive interface structure comprising a plate positioned between the hot side of the heat pump and the phase change material,
    wherein the outer cold surface of the device includes a planar surface configured for contact with the target tissue to deliver the thermal therapy.

2. The device of claim 1, wherein the thermally conductive interface structure further comprises a plurality of columns extending from the plate and into the phase change material.

3. The device of claim 1, further comprising a battery and a control processor located within the enclosure.

4. The device of claim 1, wherein the heat pump is electrically coupled to a separate implantable device containing a battery and a control processor.

5. The device of claim 1, further comprising an insulative barrier between the heat sink and the enclosure.

6. The device of claim 1, wherein the cold side of the heat pump is thermally coupled with the enclosure.

7. The device of claim 1, wherein at least one portion of the enclosure is thermally insulated from one or more other portions of the enclosure.

8. The device of claim 1, wherein the hot side of the heat pump is thermally coupled with the plate.

9. The device of claim 1, further comprising an insulative barrier extending between a periphery of the heat pump and the enclosure.

10. The device of claim 1, further comprising one or more electrical leads electrically coupled to the heat pump and extending from the enclosure.

11. The device of claim 1, further comprising one or more thermal sensors configured to detect tissue temperature.

12. The device of claim 1, wherein the enclosure includes a non-planar contoured outer surface.

13. The device of claim 1, further comprising a sensing mechanism configured for detecting when to activate the heat pump.

14. The device of claim 1, wherein the thermally conductive interface structure further comprises a plurality of columns extending: (i) from the plate, (ii) through the phase change material, and (iii) to a top surface of the phase change material adjacent to the enclosure.

15. The device of claim 1, wherein the plate is constructed of a material having a thermal conductivity in a range from 200 to 300 W/m-deg C.

16. The device of claim 1, wherein the thermally conductive interface structure further comprises a plurality of columns made of a same material as the plate.

17. The device of claim 1, wherein the planar surface configured for contact with the target tissue to deliver the thermal therapy is rectangular.

18. A method for delivering therapeutic cooling to a target tissue of a patient, the method comprising:
    cooling a portion of an outer surface of a hermetically sealed enclosure of a thermal therapy device implanted within the patient to a first temperature that is lower than a body temperature of the target tissue, wherein the cooled outer surface portion is planar and in contact with the target tissue such that heat is transferred from the target tissue to the cooled outer surface portion,
    wherein the hermetically sealed enclosure comprises: (i) a first enclosure portion comprising the cooled outer surface portion and (ii) a second enclosure portion comprising a hot outer surface portion, and wherein the first and second enclosure portions are welded to each other to form the hermetically sealed enclosure, wherein the cooling of the outer surface portion is generated by a Peltier device located within the enclosure;

conducting, by a plate positioned within the enclosure between a hot side of the Peltier device and a phase change material located within the enclosure, at least some of the heat; and absorbing, in the phase change material, at least some of the heat.

19. The method of claim 18, wherein the target tissue is an atrial tissue surface or a ventricle tissue surface.

20. The method of claim 18, wherein absorbing the at least some of the heat transferred from the target tissue in the phase change material causes at least some of the phase change material to change phases from a solid to a liquid.

* * * * *